United States Patent
Dilsky

(10) Patent No.: US 8,722,593 B2
(45) Date of Patent: May 13, 2014

(54) ALKOXYLATED THIACALIXARENES AND THE USE THEREOF AS CRUDE OIL DEMULSIFIERS

(75) Inventor: Stefan Dilsky, Gerbrunn (DE)

(73) Assignee: Clariant Finance (BVI) Limited, Tortola (VG)

( * ) Notice: Subject to any disclaimer, the term of this patent is extended or adjusted under 35 U.S.C. 154(b) by 244 days.

(21) Appl. No.: 13/394,697

(22) PCT Filed: Aug. 24, 2010

(86) PCT No.: PCT/EP2010/005186
§ 371 (c)(1),
(2), (4) Date: Mar. 7, 2012

(87) PCT Pub. No.: WO2011/029528
PCT Pub. Date: Mar. 17, 2011

(65) Prior Publication Data
US 2012/0172270 A1    Jul. 5, 2012

(30) Foreign Application Priority Data
Sep. 8, 2009 (DE) .......................... 10 2009 040 495

(51) Int. Cl.
C10M 135/34 (2006.01)
C10M 135/30 (2006.01)
C10M 135/32 (2006.01)
C07D 341/00 (2006.01)

(52) U.S. Cl.
CPC ........... *C10M 135/34* (2013.01); *C10M 135/30* (2013.01); *C10M 135/32* (2013.01); *C10M 2219/102* (2013.01); *C07D 341/00* (2013.01)
USPC .............................. 508/300; 508/569; 549/1

(58) Field of Classification Search
CPC ............. C10M 135/30; C10M 135/32; C10M 135/34; C10M 2219/102; C07D 341/00
USPC ....................................... 508/300, 569; 549/1
See application file for complete search history.

(56) References Cited

U.S. PATENT DOCUMENTS

| | | | |
|---|---|---|---|
| 4,032,514 A * | 6/1977 | Buriks et al. | ...... 525/507 |
| 4,117,031 A | 9/1978 | Macenka et al. | |
| 4,321,146 A | 3/1982 | McCoy et al. | |
| 5,401,439 A | 3/1995 | Elfers et al. | |
| 5,445,765 A | 8/1995 | Elfers et al. | |
| 6,646,016 B2 | 11/2003 | Holtrup et al. | |
| 6,936,721 B2 * | 8/2005 | Parola et al. | ...... 549/3 |
| 2004/0102586 A1 | 5/2004 | Leinweber et al. | |

FOREIGN PATENT DOCUMENTS

| | | |
|---|---|---|
| CA | 1309552 | 10/1992 |
| DE | 24 45 873 | 4/1976 |
| DE | 100 57 044 | 5/2002 |
| EP | 0 264 841 | 4/1988 |
| EP | 0 541 018 | 5/1993 |
| EP | 1 264 872 | 12/2002 |

OTHER PUBLICATIONS

International Search Report for PCT/EP2010/005186, dated Nov. 19, 2010.
"Something Old, Something New: A Discussion about Demulsifiers", T. G. Balson, pp. 226-238 in Proceedings in the Chemistry in the Oil Industry VIII Symposium, Nov. 3-5, 2003, Manchester, GB.
"Crude-Oil Emulsions: A State-Of-The-Art Review", S. Kokal, pp. 5-13, Society of Petroleum Engineers SPE 77497, 2005.
Oleg Kasyan, et al., "Synthesis, Structure and Selective Upper Rim Functionalization of Long Chained Alkoxythiacalix[4]arenes", Journal of Inclusion Phenomena and Macrocyclic Chemistry, vol. 58, No. 1-2, Nov. 22, 2006, pp. 127-132.
Akdas, H., "Molecular baskets based on tetramercaptotetrahiacalix[4]rane and tetrathiacalix[4]rane" in Tetrahedron Letters 2002, vol. 43, p. 8975-8979.
Ye, Z. F., "Synthesis and Properties of New Thiacalixarene Derivates with Palladium Ion" in J. of Inclusion Phenomena and Macrocyclic Chemistry 2001, vol. 40, p. 89-93.

* cited by examiner

*Primary Examiner* — Taiwo Oladapo
(74) *Attorney, Agent, or Firm* — Tod A. Waldrop

(57) ABSTRACT

The invention relates to compounds with the formula (II), where R is a $C_1$- to $C_{30}$-alkyl group, a $C_2$- to $C_{30}$-alkenyl group, a $C_6$- to $C_{18}$-aryl group, or a $C_7$- to $C_{30}$-alkylaryl group, AO is a $C_2$-$C_4$-alkoxy group, x is a number from 1 to 50, m is a number between 4 and 12, and to the use thereof in quantities of 0.0001 to 5% by weight relative to the oil content of the emulsion to be demulsified, for splitting water in oil emulsions.

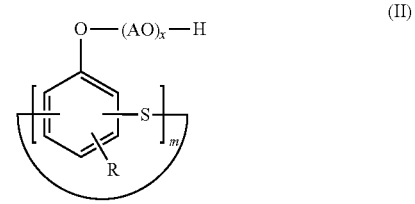

(II)

16 Claims, No Drawings

ALKOXYLATED THIACALIXARENES AND THE USE THEREOF AS CRUDE OIL DEMULSIFIERS

RELATED APPLICATION

This application is a national stage entry of PCT/EP2010/005186, filed Aug. 24, 2010, which claims priority to German application No. 102009040495.3, filed Sep. 8, 2009, which is incorporated by reference in its entirety.

The present invention relates to alkoxylated thiacalixarenes and to the use thereof for breaking water-in-oil emulsions, especially in crude-oil production.

Crude oil is recovered in the form of an emulsion with water. Before further processing the crude oil, these crude-oil emulsions have to be broken to separate them into the oil portion and the water portion. This is generally done using so-called crude-oil or petroleum emulsion breakers, or else "petroleum breakers" for short. Petroleum breakers are surface-active polymeric compounds capable of effectuating the requisite separation in the emulsion constituents within a short time.

It is mainly alkoxylated alkylphenol-formaldehyde resins, nonionic alkylene oxide block copolymers and also variants crosslinked with bisepoxides that are used as demulsifiers. Overviews are given by "Something Old, Something New: A Discussion about Demulsifiers", T. G. Balson, pp. 226-238 in *Proceedings in the Chemistry in the Oil Industry VIII Symposium*, Nov. 3-5, 2003, Manchester, GB, and also "Crude-Oil Emulsions: A State-Of-The-Art Review", S. Kokal, pp. 5-13, Society of Petroleum Engineers SPE 77497.

U.S. Pat. No. 4,321,146 discloses alkylene oxide block copolymers for breaking petroleum emulsions.

U.S. Pat. No. 5,445,765 and EP-A-0 541 018 disclose alkoxylated polyethyleneimines useful as petroleum demulsifiers.

Copolymers of hydrophobic, end group capped and partly crosslinked (meth)acrylates and hydrophilic comonomers as emulsion breakers are disclosed in EP-A-0 264 841.

U.S. Pat. No. 4,032,514 discloses the use of alkylphenol-aldehyde resins for breaking petroleum emulsions. These resins are obtainable by condensing a para-alkylphenol with an aldehyde, usually formaldehyde.

Such resins are often used in alkoxylated form, as disclosed in DE-A-24 45 873 for example. For this purpose, the free phenolic OH groups are reacted with an alkylene oxide.

In addition to the free phenolic OH groups, free OH groups of alcohols or NH groups of amines can also be alkoxylated, as disclosed in U.S. Pat. No. 5,401,439 for example.

Variants concerning alkylphenol-formaldehyde resins are disclosed in DE-A-100 57 044 and U.S. Pat. No. 6,646,016. DE-A-100 57 044 discloses the use of resins formed from alkylphenols and glyoxalic acid derivatives as emulsion breakers, while U.S. Pat. No. 6,646,016 discloses the use of condensation products of benzoic esters and amides and aldehydes for breaking crude-oil emulsions.

EP-A-1 264 872 discloses thiacalixarenes and a method of making them.

The different properties (e.g., asphaltene, paraffin and salt contents, chemical composition of the natural emulsifiers) and water fractions of various crude oils make it imperative to further develop the existing petroleum breakers. Particularly a low dosage rate and broad applicability of the petroleum breaker to be used is at the focus of economic and ecological concern as well as the higher effectivity sought. Furthermore, formaldehyde in particular is of concern as a sensitizing material, and so formaldehyde-free emulsion breakers are of particular interest.

It is an object of the present invention to develop novel petroleum breakers which are equivalent or superior to the existing alkylphenol-formaldehyde-based petroleum breakers in performance, and can be used in even lower concentrations.

Surprisingly, alkoxylated condensates of alkylphenols and elemental sulfur, which are known as thiacalixarenes, are found to give excellent performance as petroleum breakers at very low dose.

The invention accordingly provides alkoxylated thiacalixarenes obtainable by the reaction of alkylphenols of formula (I),

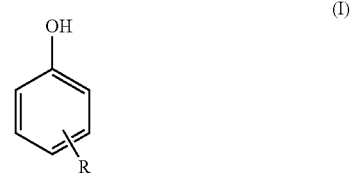

where the substituents R and OH can be ortho, meta or para relative to each other and R is a $C_1$ to $C_{30}$ alkyl, $C_2$ to $C_{30}$ alkenyl, $C_6$ to $C_{18}$ aryl or $C_7$ to $C_{30}$ alkylaryl group, with elemental sulfur and subsequent alkoxylation with $C_2$ to $C_4$ alkylene oxides.

The invention further provides compounds of formula (II)

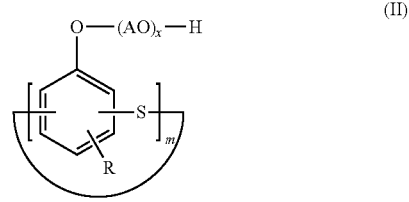

where
R is a $C_1$ to $C_{30}$ alkyl, $C_2$ to $C_{30}$ alkenyl, $C_6$ to $C_{18}$ aryl or $C_7$ to $C_{30}$ alkylaryl group,
AO is a $C_2$ to $C_4$ alkoxy group,
x is from 1 to 50,
m is between 4 and 12.

The invention further provides for the use of the compounds of formula (II) for breaking oil/water emulsions, in amounts of 0.0001% to 5% by weight, based on the oil content of the emulsion to be broken.

The invention further provides a process for breaking a water-in-oil emulsion by adding to the emulsion from 0.0001% to 5% by weight, based on the weight of the emulsion, of a compound of the formula (II).

The compounds of formula (I) are essentially chemically unitary compounds. The term "essentially" has the meaning here that the thiacalixarenes according to the invention are prepared using compounds of formula (I) in commercial purity. The resins may accordingly contain proportions of further compounds coming within formula (I), meaning more particularly incompletely removed positional isomers. This does not preclude the possibility that phenols substituted with different radicals R can be mixed to prepare the thiacalixarenes according to the invention.

The substituents R and OH are preferably in para position.
R is preferably an alkyl radical whose chain length is preferably 1 to 18 more preferably 2 to 14 and specifically 4 to 12 carbon atoms. The alkyl radicals may be linear or branched.

R is further preferably an aryl radical whose ring size is preferably 6 to 18 more preferably 6 to 12.

R is preferably an alkenyl radical whose chain length is preferably 2 to 18 more preferably 3 to 14 and specifically 4 to 12 carbon atoms. The alkenyl radicals may be linear or branched.

The thiacalixarenes useful as a precursor are preferably prepared by alkaline catalysis in accordance with the prior art, as disclosed in EP-1 264 872. Ring structures having equal numbers of phenol units and sulfur atoms are formed preferentially. The catalyst used is KOH or NaOH, which are used in amounts of 0.1% to 50% by weight, based on the reaction mixture. The solvents used are high-boiling aprotic ethers, for example tetraglyme. The condensation is carried out between 150 and 300° C., preferably 200 and 250° C., and the condensation time is generally in the range from 2 to 8 hours. The molar ratio of phenol to sulfur is in the range from 1:1 to 1:3 and preferably in the range from 1:1.3 to 1:2.3.

In a preferable embodiment, the thiacalixarenes thus formed conform to formula (III)

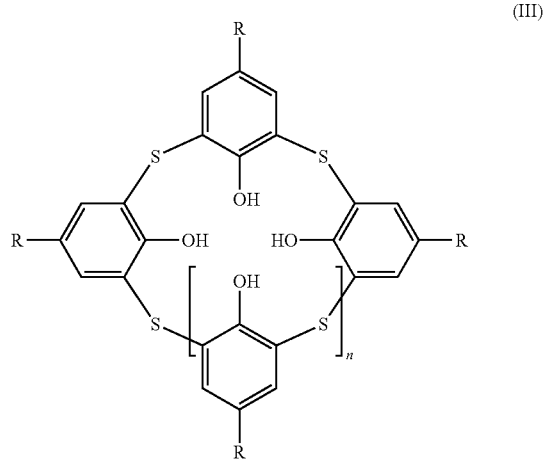

(III)

where n is 1 to 9, and

R is a $C_1$ to $C_{30}$ alkyl, $C_2$ to $C_{30}$ alkenyl, $C_6$ to $C_{18}$ aryl or $C_7$ to $C_{30}$ alkylaryl group.

The molecular weight of thiacalixarenes useful as a precursor for the alkoxylation is preferably in the range from 400 to 2500 and especially in the range from 500 to 2000 units (prior to alkoxylation).

The thiacalixarenes obtained from the condensation are then alkoxylated with a $C_2$ to $C_4$ alkylene oxide, preferably ethylene oxide and propylene oxide. The alkoxylation takes place on the free phenolic OH groups and can either be random or, as in a preferable embodiment, blockwise. Sufficient alkylene oxide is used for the average degree of alkoxylation to be between 1 and 50 alkylene oxide units per free phenolic OH group. Average degree of alkoxylation here is to be understood as meaning the average number of alkoxy units which becomes added onto each free phenolic OH group. The average degree of alkoxylation is preferably in the range from 2 to 40 and especially in the range from 3 to 30.

The number average molecular weight of the alkoxylated thiacalixarene according to the invention, obtained after condensation and alkoxylation, is preferably in the range from 500 to 50 000 units and more particularly in the range from 1000 to 20 000 units.

Alkoxylation is effected as known in the prior art, by reacting the thiacalixarenes with an alkylene oxide under elevated pressure of generally 1.1 to 20 bar at temperatures of 50 to 200° C.

A preferred aspect of the present invention is the use of alkoxylated thiacalixarenes as breakers for oil/water emulsions in petroleum production.

When used as petroleum breakers, the alkoxylated thiacalixarenes are added to the water-in-oil emulsions, preferably in solution. Aromatic or alcoholic solvents are preferred for the alkoxylated thiacalixarenes. The alkoxylated thiacalixarenes are used in amounts of 0.0001% to 5%, preferably 0.0005% to 2%, especially 0.0008% to 1% and specifically 0.001% to 0.1% by weight, based on the oil content of the emulsion to be broken.

EXAMPLES

Example 1

Reaction of p-Tert-Butylphenol with Sulfur

A 500 ml stirred flask equipped with a stirrer, a water separator, an internal thermometer and a nitrogen inlet was initially charged with 150.0 g of p-tert-butylphenol (M=150), 60.0 g of sulfur (M=32), 20.0 g of 50% aqueous sodium hydroxide solution and 50.0 g of tetraethylene glycol dimethyl ether (tetraglyme). Under agitation and nitrogen purge, the mixture is gradually, over 4 hours, brought to 230° C. and maintained at this temperature for a further 2 hours. The water from the catalyst is removed via the separator, and the hydrogen sulfide formed is routed out through a gas scrub bottle containing alkaline hydrogen peroxide solution. The molar mass of the polymer was analyzed via GPC (reference: polyethylene glycol). The yield after removal of solvent in vacuo is 180.5 g.

Example 2

Reaction of p-Isononylphenol with Sulfur

A 500 ml stirred flask equipped with a stirrer, a water separator, an internal thermometer and a nitrogen inlet was initially charged with 150.0 g of p-isononylphenol (M=220), 40.0 g of sulfur (M=32), 13.5 g of 50% aqueous sodium hydroxide solution and 35.0 g of tetraethylene glycol dimethyl ether (tetraglyme). Under agitation and nitrogen purge, the mixture is gradually, over 4 hours, brought to 230° C. and maintained at this temperature for a further 2 hours. The water from the catalyst is removed via the separator, and the hydrogen sulfide formed is routed out through a gas scrub bottle containing alkaline hydrogen peroxide solution. The molar mass of the polymer was analyzed via GPC (reference: polyethylene glycol). The yield after removal of solvent in vacuo is 171.0 g.

Example 3

Reaction of p-Phenylphenol with Sulfur

A 500 ml stirred flask equipped with a stirrer, a water separator, an internal thermometer and a nitrogen inlet was initially charged with 150.0 g of p-phenylphenol (M=170), 55.0 g of sulfur (M=32), 18.0 g of 50% aqueous sodium hydroxide solution and 50.0 g of tetraethylene glycol dimethyl ether (tetraglyme). Under agitation and nitrogen purge, the mixture is gradually, over 4 hours, brought to 230° C. and maintained at this temperature for a further 2 hours. The water from the catalyst is removed via the separator, and the hydrogen sulfide formed is routed out through a gas scrub bottle containing alkaline hydrogen peroxide solution. The molar mass of the polymer was analyzed via GPC (reference: polyethylene glycol). The yield after removal of solvent in vacuo is 176.5 g.

Example 4

Reaction of p-Tert-Butylphenol and p-Isononylphenol with Sulfur

A 500 ml stirred flask equipped with a stirrer, a water separator, an internal thermometer and a nitrogen inlet was initially charged with 90.0 g of p-tert-butylphenol (M=150), 65.0 g of p-isononylphenol (M=220), 55.0 g of sulfur (M=32), 18.0 g of 50% aqueous sodium hydroxide solution and 50.0 g of tetraethylene glycol dimethyl ether (tetraglyme). Under agitation and nitrogen purge, the mixture is gradually, over 4 hours, brought to 230° C. and maintained at this temperature for a further 2 hours. The water from the catalyst is removed via the separator, and the hydrogen sulfide formed is routed out through a gas scrub bottle containing alkaline hydrogen peroxide solution. The molar mass of the polymer was analyzed via GPC (reference: polyethylene glycol). The yield after removal of solvent in vacuo is 178.0 g.

Alkoxylation of Thiacalixarenes

Ethoxylation

The thiacalixarenes described above or propoxylates thereof were introduced into a 1 l glass autoclave and the pressure in the autoclave was adjusted with nitrogen to about 0.2 bar superatmospheric. The pressure was gradually raised to 140° C. and, on attainment of this temperature, the pressure was again adjusted to 0.2 bar superatmospheric. Thereafter, the desired quantity of ethylene oxide was dosed in at 140° C. while the pressure should not exceed 4.5 bar. On completion of the ethylene oxide addition the system was allowed to react further at 140° C. for 30 minutes.

Propoxylation

The thiacalixarenes described above or ethoxylates thereof were introduced into a 1 l glass autoclave and the pressure in the autoclave was adjusted with nitrogen to about 0.2 bar superatmospheric. The pressure was gradually raised to 130° C. and, on attainment of this temperature, the pressure was again adjusted to 0.2 bar superatmospheric. Thereafter, the desired quantity of ethylene oxide was dosed in at 130° C. while the pressure should not exceed 4.0 bar. On completion of the ethylene oxide addition the system was allowed to react further at 130° C. for 30 minutes.

Determination of Breaking Efficacy of Petroleum Emulsion Breakers

Emulsion breaker efficacy was determined by determining water separation from a crude-oil emulsion per unit time and also the dehydration of the oil. To this end, breaker glasses (conically tapered, graduated glass bottles closeable with a screw top lid) were each filled with 100 ml of the crude-oil emulsion, a defined amount of the emulsion breaker was in each case added with a micropipette just below the surface of the oil emulsion, and the breaker was mixed into the emulsion by intensive shaking. Thereafter, the breaker glasses were placed in a temperature control bath (50° C.) and water separation was tracked.

On completion of emulsion breaking, samples of the oil were taken from the top part of the breaker glass (top oil). A 15 ml centrifuge vial (graduated) is filled with 5 ml of Shellsol A 150 ND and 10 ml of oil sample, the vial is shaken by hand to achieve commixing, and is then centrifuged at 1500 rpm for 5 minutes. The water volumes read off are multiplied by a factor of 10 and the values thus determined are reported as percent water. In this way, the novel breakers were assessed in terms of water separation and also oil dehydration.

Breaking Effect of Breakers Described

Origin of crude-oil emulsion: Hebertshausen, Germany
Water content of emulsion: 48%
Demulsifying temperature: 50° C.

The efficacy of the alkoxylated thiacalixarenes as emulsion breakers compared with Dissolvan® 3279-1c. (an ethoxylated alkali-condensed p-isononyl/p-tert-butyl-phenol-formaldehyde resin) is shown in the following tables.

| Example | Dosage rate [ppm] | 10 | 20 | 30 | 45 | 60 | 120 | Water in top oil [%] |
|---|---|---|---|---|---|---|---|---|
| product of 1 + 2.0 mol of EO | 40 | 3 | 18 | 30 | 38 | 44 | 45 | 1.0 |
| product of 1 + 3.0 mol of EO | 40 | 7 | 30 | 39 | 43 | 43 | 45 | 2.0 |
| product of 2 + 2.5 mol of EO | 40 | 1 | 13 | 23 | 34 | 39 | 41 | 1.5 |
| product of 2 + 3.5 mol of EO | 40 | 4 | 26 | 35 | 38 | 42 | 43 | 2.5 |

-continued

| Example | Dosage rate [ppm] | 10 | 20 | 30 | 45 | 60 | 120 | Water in top oil [%] |
|---|---|---|---|---|---|---|---|---|
| product of 2 + 6.5 mol of PO | 40 | 0 | 8 | 18 | 30 | 33 | 36 | 5.0 |
| product of 3 + 3.0 mol of EO | 40 | 3 | 20 | 29 | 34 | 38 | 40 | 2.0 |
| product of 3 + 1.0 mol of PO + 3.0 mol of EO | 40 | 2 | 17 | 29 | 36 | 40 | 42 | 3.5 |
| product of 4 + 2.0 mol of EO | 40 | 3 | 13 | 27 | 39 | 43 | 45 | 2.0 |
| product of 4 + 2.5 mol of EO | 40 | 5 | 22 | 32 | 40 | 44 | 44 | 3.0 |
| Product from 4 + 3.0 mol of EO | 40 | 8 | 35 | 38 | 40 | 42 | 43 | 4.0 |
| Product from 4 + 1.0 mol of PO + 3.5 mol of EO | 40 | 4 | 20 | 29 | 38 | 40 | 42 | 2.5 |
| Product from 4 + 2.0 mol of PO | 40 | 2 | 9 | 25 | 35 | 37 | 40 | 3.0 |
| Dissolvan 3279-1c. | 60 | 5 | 32 | 36 | 38 | 42 | 42 | 3.5 |

What is claimed is:

1. A process for breaking a water-in-oil emulsion comprising the step of adding at least one alkoxylated thiacalixarene of formula (II)

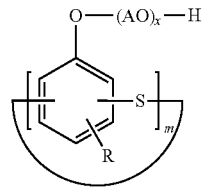

(II)

where
R is a $C_1$ to $C_{30}$ alkyl, $C_2$ to $C_{30}$ alkenyl, $C_6$ to $C_{18}$ aryl or $C_7$ to $C_{30}$ alkylaryl group,
AO is a $C_2$ to $C_4$ alkoxy group,
x is from 1 to 50,
m is between 4 and 12,
in an amount of 0.0001% to 5% by weight, based on the oil content of the emulsion to be broken, to the water-in-oil emulsion.

2. A process for breaking a water-in-oil emulsion according to claim 1, wherein R and the phenolic OH group are in para position.

3. A process for breaking a water-in-oil emulsion according to claim 1, wherein R is an alkyl, aryl or alkenyl radical of 4 to 12 carbon atoms.

4. A process for breaking a water-in-oil emulsion according to claim 1, wherein the degree of alkoxylation is between 1 and 30.

5. A process for breaking a water-in-oil emulsion according to claim 1, wherein m is from 4 to 12.

6. A process for breaking a water-in-oil emulsion according to claim 1, wherein the molecular weight of the alkoxylated thiacalixarene is between 1000 and 20 000.

7. A compound of formula (II)

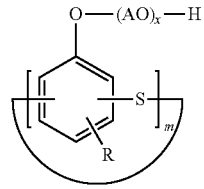

(II)

where
R is a $C_1$ to $C_{30}$ alkyl, $C_2$ to $C_{30}$ alkenyl, $C_6$ to $C_{18}$ aryl or $C_7$ to $C_{30}$ alkylaryl group,
AO is a $C_2$ to $C_4$ alkoxy group,
x is from 1 to 50,
m is between 4 and 12.

8. The compound according to formula (IV)

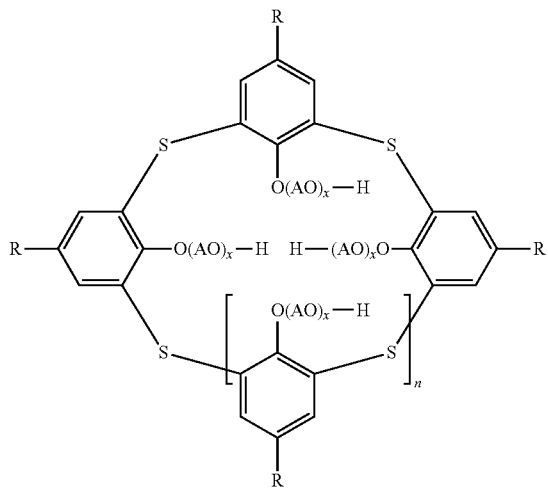

(IV)

where
R is a $C_1$ to $C_{30}$ alkyl, $C_2$ to $C_{30}$ alkenyl, $C_6$ to $C_{18}$ aryl or $C_7$ to $C_{30}$ alkylaryl group,
AO is a $C_2$ to $C_4$ alkylene oxide group,
x is from 1 to 50,
n is between 1 and 9.

9. The compound according to claim 7 wherein R is an alkyl, aryl or alkenyl radical of 4 to 12 carbon atoms.

10. The compound according to claim 7, wherein AO is a block of ethylene oxide, a block of propylene oxide or a block of ethylene oxide and a block of propylene oxide.

11. The compound according to claim 7, wherein x is from 1 to 30.

12. A process for breaking a water-in-oil emulsion comprising the step of adding to the emulsion from 0.0001% to 5% by weight, based on the weight of the emulsion, of at least one compound according to claim 7.

13. The compound according to claim 8, wherein R is an alkyl, aryl or alkenyl radical of 4 to 12 carbon atoms.

14. The compound according to claim 8, wherein AO is a block of ethylene oxide, a block of propylene oxide or a block of ethylene oxide and a block of propylene oxide.

15. The compound according to claim 8, wherein x is from 1 to 30.

16. A process for breaking a water-in-oil emulsion comprising the step of adding to the emulsion from 0.0001% to 5% by weight, based on the weight of the emulsion, of at least one compound according to claim 8.

* * * * *